United States Patent [19]
Yelderman

[11] Patent Number: 5,193,543
[45] Date of Patent: Mar. 16, 1993

[54] METHOD AND APPARATUS FOR MEASURING ARTERIAL BLOOD CONSTITUENTS

[75] Inventor: Mark Yelderman, Plano, Tex.

[73] Assignee: Critikon, Inc., Tampa, Fla.

[21] Appl. No.: 865,774

[22] Filed: Apr. 6, 1992

Related U.S. Application Data

[63] Continuation of Ser. No. 510,301, Apr. 16, 1990, abandoned, which is a continuation-in-part of Ser. No. 940,860, Dec. 12, 1986, abandoned, which is a continuation-in-part of Ser. No. 946,492, Dec. 24, 1986, abandoned.

[51] Int. Cl.$^5$ .............................................. A61B 5/02
[52] U.S. Cl. ................................... 128/633; 128/666; 356/41
[58] Field of Search ....................... 128/633, 665–666; 356/41

[56] References Cited

U.S. PATENT DOCUMENTS

| | | | |
|---|---|---|---|
| 3,463,142 | 8/1969 | Harte | 128/2 |
| 3,647,299 | 3/1972 | Lavallee | 356/41 |
| 3,980,075 | 9/1976 | Heule | 128/2.05 R |
| 3,993,047 | 11/1976 | Peek | 128/2.05 P |
| 3,994,590 | 11/1976 | DiMartini et al. | 356/178 |
| 3,998,550 | 12/1976 | Konishi et al. | 356/39 |
| 4,001,667 | 1/1977 | Bober | 323/1 |
| 4,013,067 | 3/1977 | Kresse et al. | 128/2.05 R |
| 4,086,915 | 5/1978 | Kofsky et al. | 128/2 L |
| 4,167,331 | 9/1979 | Nielsen | 356/39 |
| 4,266,554 | 5/1981 | Hamaguri | 128/633 |
| 4,353,152 | 10/1982 | O'Connor et al. | 128/689 |
| 4,356,448 | 10/1982 | Brogardh et al. | 324/244 |
| 4,407,290 | 10/1983 | Wilber | 128/633 |
| 4,446,715 | 5/1984 | Bailey | 73/1 R |
| 4,555,179 | 11/1985 | Langerhole et al. | 356/342 |
| 4,603,700 | 8/1986 | Nichols et al. | 128/633 |
| 4,623,248 | 11/1986 | Sperinde | 356/41 |
| 4,723,554 | 1/1988 | Oman et al. | 128/664 |
| 4,807,631 | 2/1989 | Hersh et al. | 128/633 |
| 4,848,901 | 7/1989 | Hood, Jr. | 356/41 |
| 4,863,265 | 9/1989 | Flower et al. | 128/633 |

FOREIGN PATENT DOCUMENTS

| | | |
|---|---|---|
| 0102816A2 | 3/1984 | European Pat. Off. |
| 0104771A2 | 4/1984 | European Pat. Off. |
| 0160768A1 | 11/1985 | European Pat. Off. |
| 2136823 | of 0000 | Fed. Rep. of Germany |
| 86/00514 | 7/1985 | PCT Int'l Appl. |

OTHER PUBLICATIONS

Janssen, F. J., "The Principle Design and Features of a New Hb-Oximeter", Medical & Biological Engineering, vol. 10, No. 1, Jan. 1972, pp. 9–22, Pergamon Press.

Graf, Rudolf F., Modern Dictionary of Electronics, Howard Sams & Co., Inc., Indianapolis, 3rd Bd., 1970, p. 498.

Schmitt, Joseph Michael, "Optical Measurement of Blood Oxygen by Implantable Telemetry", Standard Electronics Laboratories, 31 (Feb. 1986), Technical Report G-558-15, Stanford Electronics Laboratories, Dept. of Electrical Engineering, Stanford University.

Primary Examiner—Lee S. Cohen
Assistant Examiner—Robert L. Nasser, Jr.
Attorney, Agent, or Firm—Woodcock Washburn Kurtz Mackiewicz & Norris

[57] ABSTRACT

A method and apparatus for non-invasively measuring blood constituent concentration and particularly the oxygen saturation of arterial blood. The apparatus includes at least one light source directed to a tissue area of a patient, such as a finger or earlobe. A photodetector receives emitted light passing through the sample, and a receiver circuit analyzes the data and produces an output which is proportional to the oxygen content of blood. The light source is modulated onto a preselected carrier frequency and the receiver circuit is tuned to the carrier frequency so that undesired signals such as ambient light can be filtered out leaving only the signals created by the emitted light passing through the tissue at the light source frequency. The oxygen content is then calculated using the patient's known red cell count, thereby correcting the final saturation value for patient anemia. Moreover, the calculation for oxygen saturation incorporates red cell scattering parameters for increased accuracy in clinical environments.

43 Claims, 5 Drawing Sheets

METHOD AND APPARATUS FOR MEASURING ARTERIAL BLOOD CONSTITUENTS

This is a continuation of application Ser. No. 07/510,301, filed Apr. 16, 1990, and now abandoned, which is a continuation in part of Ser. No. 06/940,860 filed Dec. 12, 1986 now abandoned, and Ser. No. 06/946,492 and now abandoned filed Dec. 24, 1986.

BACKGROUND OF THE INVENTION

1. Field of Invention

This invention relates to a method and apparatus for noninvasively measuring blood constituents and, more particularly, to a method and apparatus for detecting variations in the detected amplitude of one or more wavelengths of light which are transmitted through body tissue to measure the concentration of blood constituents such as saturated hemoglobin oxygen and for compensating for ambient light interference which adversely affects such determinations.

2. Description of the Prior Art

The determination of blood oxygen concentrations and the concentrations of other blood constituents such as injected dyes has become increasingly interesting to physicians and of increasing importance in the practice of clinical medicine. Generally, it is known to use spectrophotometric techniques to measure arterial hemoglobin oxygen saturation. For example, various blood constituent measuring devices and methods using non-invasive techniques are known whereby emitted light is passed through the sample, or reflected therefrom, and then detected by light sensors. Variations in the detected light at various wavelengths are then used to determine arterial oxygen saturation and/or pulse rates. Such devices and/or methods are shown, for example, in U.S. Pat. Nos. 4,407,290; 4,266,554; 4,167,331; 4,086,915; 3,998,550; and 3,647,299; and European patent Nos. EP 0 104 771 A3 and EP 0 102 816 A3.

However, such prior art oximetry devices and methods are typically inaccurate, for significant errors are induced in clinical oximetry if the classical absorption equation (Bier's Law) is used to calculate the saturation of oxygen as applicable to pure hemoglobin. The methods disclosed in U.S. Pat. Nos. 4,167,331; 3,998,550; 4,086,915; and 4,266,554 do not compensate such errors. As a partial solution to this problem, however, other patents teach the use of a mathematical approximation to Bier's Law by using ratios of the pulsating absorbance and the non-pulsating absorbance components of each of several wavelengths of transmitted light, as in U.S. Pat. Nos. 4,407,290 and 3,647,299 and European Patent Nos. EP 0 104 771 A3 and EP 0 102 816 A3, for example. Also, because the light absorption of tissue does not exactly correspond to that predicted by Bier's Law, some type of empirical calibration has been performed as taught in U.S. Pat. Nos. 4,407,290; 4,167,331; and 4,086,915.

The derivation of the absorbance in the pulsating component may be performed in different ways. One technique relies upon the quantitative measurement in the change in absorbance at each wavelength, as in U.S. Pat. No. 4,407,290 and European patent Nos. EP 0 104 771 A3 and Ep 0 102 816 A3. It is also known that the derivative of the change in absorbance and a peak to peak measurement of the pulsating absorbance component may be used to calculate the Oxygen content of arterial blood, as taught in U.S. Pat. Nos. 4,407,290 and 4,167,331.

In addition, it is known that a single light detector may be used. However, when a single light detector is used, the detected light for each wavelength must be separated. This is accomplished by using time separation and synchronous detection as taught in U.S. Pat. Nos. 4,407,290; 4,266,554; and 3,647,299, for example. However, because the light detectors also detect ambient light, some type of ambient light rejection technique is normally employed. One technique is to use four clock states and to allow for the subtraction of ambient light, as taught in U.S. Pat. Nos. 4,407,290 and 4,266,554. Another technique is to remove the non-pulsating absorbance component since ambient light is usually a non-pulsating absorbance frequency, as taught in U.S. Pat. Nos. 4,167,331 and 3,998,550. These techniques consider the ambient light to have a constant amplitude.

However, the techniques and devices disclosed in the above-referenced patents are not completely satisfactory and are deficient in several areas for the following reasons. Namely, Bier's Law and/or the use of empirical estimates usually only approximate the oxygen content of blood in living tissues in clinical environments. Moreover, prior art techniques for removing ambient light and motion artifacts are unsatisfactory and generally produce decreased signal to noise ratios and increased errors in the clinical measurements because up to fifty percent of the duty cycle is devoted to making ambient light measurements. In addition, techniques using synchronous detectors are not completely satisfactory since they require wide bandwidth AC amplifiers and because they also may devote a significant portion of the duty cycle, as much as 50%, to measuring the ambient light rather than the desired absorbance changes. Furthermore, the wide bandwidth requirements of the prior art devices render such devices more susceptible to frequency interference such as BOVIE interference, which is a type of system noise produced by electrical surgical devices such as coagulators and cauterizers. It typically affects the frequency range of 0.5 to 5 MHZ, but it can be found even in direct current. Although there is less energy in frequencies between DC and 0.5 MHZ, there is still enough energy to potentially cause interference which impairs the performance of many prior art devices. Previous embodiments also frequently require an analog channel for each wavelength and require that these channels be matched over the bandwidth. The resulting analog requirements may be so stringent as to require that both channels have a "normalized" DC output, as in U.S. Pat. No. 4,407,290.

Thus, although blood constituent measuring devices and methods have heretofore been suggested and have achieved some success, a need still exists for a device and method for more accurately measuring blood constituents such as oxygen saturation of blood in patients, particularly anemic patients and those with blood conditions such as low red blood cell counts. These blood counts are different from the assumed counts upon which the factory "presets" are based, and accordingly, correcting the blood counts to account for patient anemia in the saturation equations, for example, could be a critical factor in keeping an anemic's brain and heart alive during surgery. Moreover, there is also a need for a device which is less sensitive to other types of interference, such as BOVIE interference, which can virtually interrupt oximetry at critical times during an operation.

The present invention has been designed to meet these needs.

SUMMARY OF THE INVENTION

A novel blood constituent measuring apparatus and method are provided which exhibit an excellent signal to noise ratio and improved resistance to interference from ambient artificial light, BOVIE interference, and the like by using AM modulation/demodulation techniques. This is accomplished by driving one or more light sources with a driving signal which does not exhibit a frequency which is present in the artificial light environment of the operating room. The frequencies of each light source are then AM modulated onto the light transmitted through the body tissue, and the transmitted light is attenuated according to the blood constituent concentrations at that particular time. In addition, since the amount of blood constituents varies from systole to diastole to systole, the transmitted light signal attenuation varies, and hence, the transmitted signal is modulated. The detected light is then received by a receiver Which is tuned to the preselected driving signal's frequency. The detected signal is then demodulated to produce the output at the frequency of each light source. As a result, both light sources may be concurrently transmitted through the body tissue so that no portion of the duty cycle must be devoted to measuring ambient light, and as a result, narrow bandpass filters may be employed at the receiver so as to reduce BOVIE interference.

The present invention also provides novel techniques for determining and displaying pulse and oxygen saturation values. Blood oxygen levels are calculated using equations which include red cell scattering parameters, and in accordance with the invention, the measurements may be corrected for abnormal red cell counts. The device of the invention also utilizes other novel signal processing techniques, including digital analysis and interpolation of temporally distinct detected light amplitudes in order to reduce the effects of interference.

It is, therefore, an object of this invention to provide a blood constituent measuring device and method.

It is another object of this invention to provide a blood constituent measuring device and method capable of determining the oxygen saturation of arterial blood in relation to the fraction of red blood cells per unit volume of whole blood.

It is still another object of this invention to provide a blood constituent measuring device and method that can provide an output which indicates an arterial pulse.

It is still another object of this invention to provide a blood constituent measuring device and method that rejects motion artifacts by subtracting extraneously detected data from a detected pulse data reading.

It is still another object of this invention to provide a blood constituent measuring device and method that calculates the oxygen saturation of arterial blood using red blood cell absorbance and scattering parameters.

With these and other objects in view, which will become apparent to one skilled in the art as the description proceeds, this invention resides in the novel construction, combination, arrangement of parts, and methods substantially as hereinafter described and more particularly defined by the attached claims.

BRIEF DESCRIPTION OF THE DRAWINGS

The accompanying drawings illustrate a complete embodiment of the invention according to the best mode so far devised for the practical application of the principles thereof, and in which:

FIG. 7 is an exemplary bar graph showing a room light spectrum of the estimated amplitudes of interfering ambient artificial light in a hypothetical environment where the power line frequency is a nominal 60 cps and the actual relative amplitudes of such interference and their frequencies vary somewhat depending upon power line frequency, lighting source, and the like.

DETAILED DESCRIPTION OF THE INVENTION

The following description is provided to enable any person skilled in the medical and electronic fields to make and use the invention and to set forth the best mode contemplated by the inventor of carrying out his invention. Various modifications, however, will remain readily apparent to those skilled in the art without departing from the generic principles of the present invention as defined specifically herein. Although a relatively economical and easily manufactured non-invasive blood constituent measuring device will be described, the scope of this disclosure is only to be limited by the attached claims.

Generally, the invention herein described includes at least one light source driven by a preselected driving signal, which source is placed in proximity to a patient's body tissue so that light may be directed therethrough; a photodetector for receiving the light so transmitted through that tissue; and a receiver circuit tuned to the driving frequency of the light source. The device of the invention effectively excludes ambient light and limits BOVIE interference and system noise by driving the light source with a driving signal having a frequency not found in the ambient light environment and by modulating the light source frequency with the preselected driving signal. Moreover, processing means are provided for processing the receiver circuit output to calculate blood saturation using scattering parameters which are proportional to the red cell count in the tissue.

Operation of the process of the invention will now be described with respect to FIGS. 1 and 2, and a specific embodiment of the apparatus of the invention then will be described with respect to FIGS. 3-6.

Figure 1:
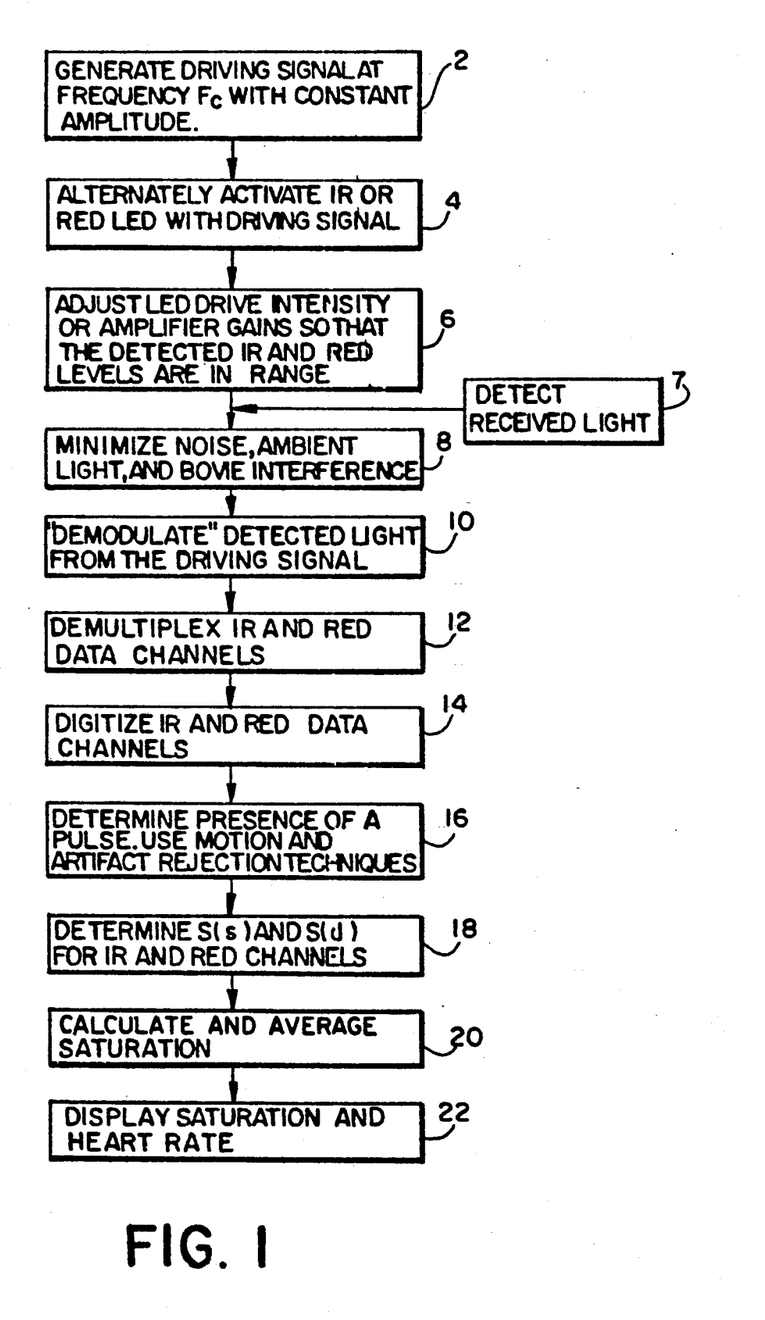
FIG. 1 is a flow diagram of a process for measuring blood constituents in accordance with the invention.

FIG. 1 shows a flow diagram of an embodiment of the process of measuring blood constituents in accordance with the invention. As shown, a driving signal having a pre-selected frequency $F_c$ and constant amplitude is generated at step 2 and is used to alternately activate an infrared and/or red light emitting diode at step 4. The frequency $F_c$ acts as a carrier frequency for the infrared and red light passing through the body tissue. An adjustment of the light emitting diode's drive intensity and/or amplifier gains can be made at step 6 so that the detected infrared and/or red light levels 7 are within the range of the analog to digital converters used in the receiver hardware. Noise, ambient light, and BOVIE interference in the detected light levels are then minimized at step 8, and the resulting detected light signal is then demodulated from the driving signal at step 10. Demultiplexing of the infrared and red data channels is then accomplished at step 12, and the resulting outputs of step 12 are digitized at step 14. The data is then processed at step 16 to determine the presence of a pulse by implementing motion and artifact rejection techniques. Saturation values for the systolic and diastolic are then calculated for each wavelength of light at step 18, and an average value for the saturation is determined at step 20. Finally, the saturation and heart rate values are displayed at step 22.

Figure 2:
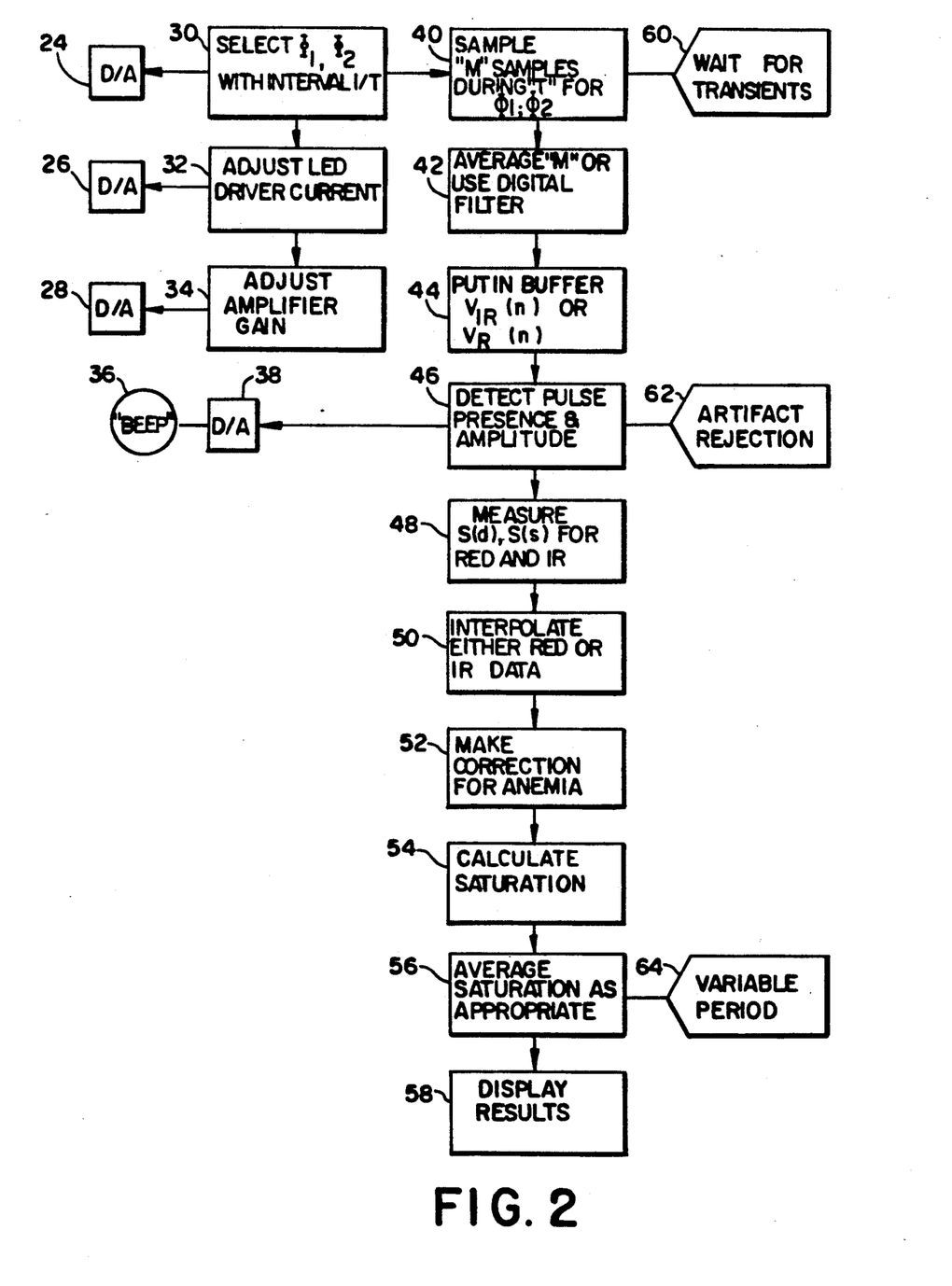
FIG. 2 is a flow diagram of a process for conducting blood oximetry in accordance with the invention, including the steps of sampling light intensity readings, storing the readings, and calculating the saturation values for hemoglobin in a patient's blood.

FIG. 2 shows a flow diagram of a process for conducting blood oximetry whereby the driving signal preferably has a uniform amplitude and frequency. Preferably, a square or sine wave sum of two or more sine waves or other periodic or nonperiodic repetitive waveform is selected as the driving signal to drive a pair of light emitting diodes for a duration T at a pre-determined clock state, designated "$\Phi_1$" or "$\Phi_2$" at step 30. The digital value output at step 30 is converted into an analog signal at D/A converter 24 for application to the oximeter for this purpose. Adjustments to the diodes, driver current and the oximeter's amplifier gain are made at steps 32 and 34, respectively, and respectively applied to the diodes of the oximeter via D/A converters 26 and 28. Then, before data points representing transmitted light values are sampled at step 40, system transients are allowed to settle at step 60. The delay necessary to overcome transients in the waveform during a given clock state will vary according to the wave generating circuit used and the amount of duty cycle required for measuring data points. In a preferred embodiment, no more than 25% of the waveform generated by the driver circuit should be used for transient settling. Preferably, less than 10%, and most preferably, less than 5% of the waveforms should be allocated for waiting for transients to settle. Alternatively, the settling time can be terminated when the transient amplitude comprises less than 1%, and preferably less than 0.1%, of the amplitude of the theoretical waveform. The sample points designated as "M" can then be either averaged or filtered by using a digital filter at step 42. The averaged or filtered data points are then placed into a buffer at step 44 for enhanced signal to noise ratios and better analog to digital resolution.

The presence and amplitude of the driving signal pulse is detected in step 46 once artifact rejection is performed at step 62. If a pulse is detected, this is so indicated by causing an audible alarm (or "beep") at alarm 36 after D/A conversion at D/A converter 38. The light intensity readings for the diastole and systole at the preferred red and infrared wavelengths are then determined at step 48. Values at step 48 may be at peaks or at other times in the cycle, but should be measured or estimated at a synchronous point in time. Since alternate clock states are preferred, an interpolation at step 50 is used for this purpose. In other words, by interpolating measured values of the light detected from one light-emitting diode to estimate a detection value when the diode is not illuminated, the device can render the clock states, $\Phi_1$ and $\Phi_2$, synchronous. A simple trigonometric interpolation is sufficient for this purpose.

An anemia correction calculation is then made at step 52. The correction for anemia is made by incorporating into the saturation calculations a factor "$\eta$" which is equivalent to the fraction of red cells per unit volume of whole blood which is calculated from the hemoglobin concentration, as will be described in more detail below. Once the anemia correction calculation is made, the saturation value "S" may be calculated at step 54. An average saturation value may be calculated as appropriate at step 56 when a variable period 64 is used, and the saturation results are then displayed at step 58.

Figure 3:
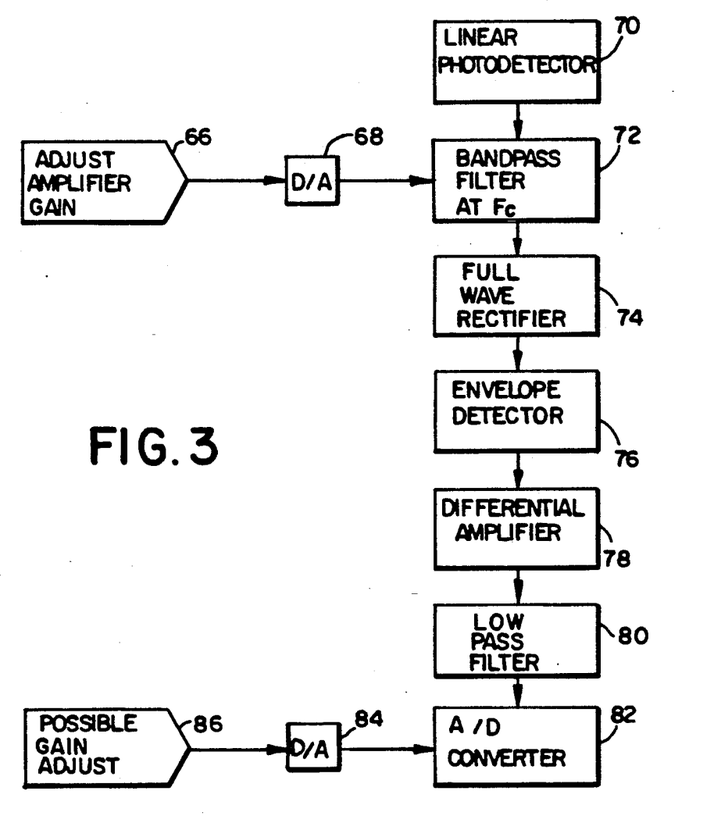
FIG. 3 is a block diagram of an embodiment of the detector and receiver circuitry in accordance with the invention, whereby the amplifier gain of the receiver may be adjusted.

As shown in FIG. 3, the amplifier gain of the receiver may be adjusted by applying the calculated adjustment determined at step 66 to the amplifier via digital to analog converter 68. The gain adjustment is made in the bandpass filter element 72 as shown. This bandpass filter 72 receives the output from the linear photodetector 70, which receives the transmitted infrared and red light signals and it operates with the full wave rectifier 74 and envelope detector 76 to form an AM demodulator for demodulating the detected signals corresponding to the red and infrared light signals from the carrier frequency $F_c$ in a manner known by those skilled in the electrical arts. In particular, these hardware elements carry out the process steps of eliminating interference and demodulating the detected light values from the driver frequency $F_c$, described above as process steps 8 and 10 of FIG. 1. A differential amplifier 78 then adds both parts of the envelope detector's output together, and the output of the differential amplifier 78 is then fed into a low pass filter 80 to eliminate ripple from the sum so as to generally improve the signal to noise ratio. The preferred embodiment also permits a possible gain adjustment (for calibration) at step 86 by applying an adjustment value via digital to analog converter 84 so as to keep the analog signal from low pass filter 80 calibrated to the analog to digital converter 82.

Figure 4:
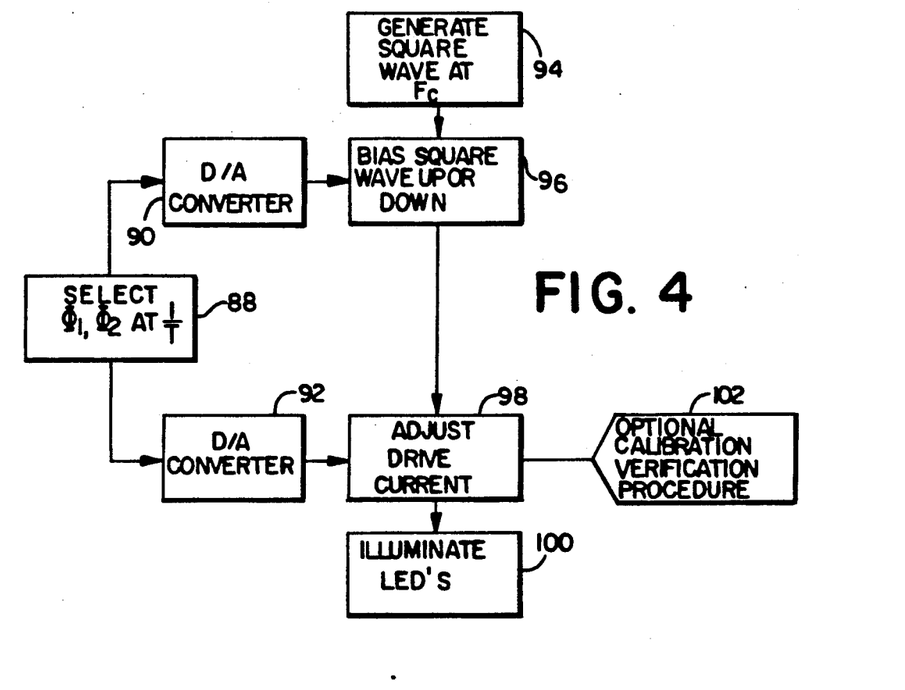
FIG. 4 is a block diagram of diode driver circuitry in which a preferred square wave driving signal is generated for driving a light-emitting diode, with optional adjustment to drive current and an optional calibration verification procedure.

FIG. 4 illustrates a diagram of the driver of the invention. As shown, a driving signal having a preselected waveform, such as a square wave at frequency $F_c$, is generated at step 94 which corresponds to process step 2 of FIG. 1. The resulting driver waveform can be biased up or down at step 96 so as to drive back to back LEDs. This biasing step may also be replaced by a switch which alternatively drives each light emitting diode. The clock state selected at step 88 (corresponding to step 30 of FIG. 2) is applied through digital to analog converters 90 and 92 to determine the duration of excitation of the light emitting diodes, and the drive current is appropriately adjusted at step 98 in accordance with the duration. The intensities of the illuminated light emitting diodes are thereby adjusted at step 100. In addition, an optional calibration verification procedure may be implemented at step 102 for verifying calibration of the driver.

Thus, during operation, when only one driving signal is used to drive two light-emitting diodes, the light-emitting diodes are driven alternatingly by that signal. The duration of excitation of each light-emitting diode is known as the clock-state and is designated as "T". If two light-emitting diodes are used, two clock-states are selected and are designated as $\Phi_1$ and $\Phi_2$. It is contemplated that the light-emitting diodes can be driven using signals such as decaying waveforms or other coded waveforms, such as non-periodic repetitive waveforms or the sum of two or more sine waves of different frequencies. However, these are not presently preferred since tuning the recurring means to, or decoding, those waveforms is somewhat more complicated. In any event, the driving signal is selected so as not to substantially overlap with the substantial artificial light amplitudes in the intended location of use to create an error problem. Preferably, the light-emitting diodes are also kept as bright as possible to improve the signal to noise ratio of the device. In addition, since at least one light-emitting diode may require adjusting, and since two wavelengths are desired, the light-emitting intensities are intentionally not adjusted to be equal.

Figure 5:
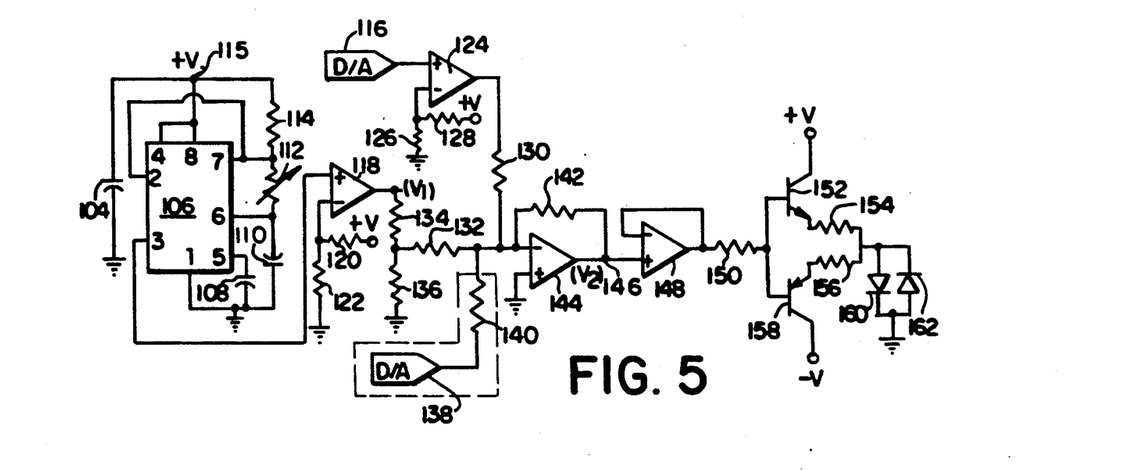
FIG. 5 is a schematic diagram of an embodiment of the light emitting diode driver circuitry in accordance with a preferred embodiment.

A detailed embodiment of a light-emitting diode driver for implementing the process of FIGS. 1 and 2 in accordance with the invention is shown in FIG. 5. As shown, an integrated timing circuit 106, such as a "555" timer, may be used to generate the driver frequency. The configuration of FIG. 5 produces a uniform square wave at 47 kHz by appropriately selecting the values of capacitors 104, 108 and 110 and resistors 112 and 114. The timer is connected to power +V at 115. Of course, other acceptable frequencies besides 47 kHz in excess of 1 kHz or 5 kHz may be used, and frequencies of greater than about 10 kHz and 40 kHz are favored. Preferably, the carrier frequency is as high as possible to optimize settling times of the circuitry. A driving signal that varies with the intensity of the light source can also be favorably used.

On the other hand, as noted above, it may also be desirable to choose frequencies which are located below the frequency of the ambient light or in-between the harmonics of the ambient light. As a minimum requirement, "a frequency not substantially present in the ambient light" means that the frequency does not correspond to an ambient light frequency having an amplitude which comprises greater than 1% of the amplitude of the ambient light. Moreover, "in-between frequencies" may be defined as within a range delineated by two principle harmonic frequencies, plus or minus 10% of the harmonic frequencies. More preferably, however, the driver frequency falls within a range defined by two principal harmonic frequencies of the ambient light, plus or minus 25% of the principal harmonic frequency, and most preferably the driver frequency is chosen to be at a point half way between two consecutive principal harmonic frequencies.

Figure 7:
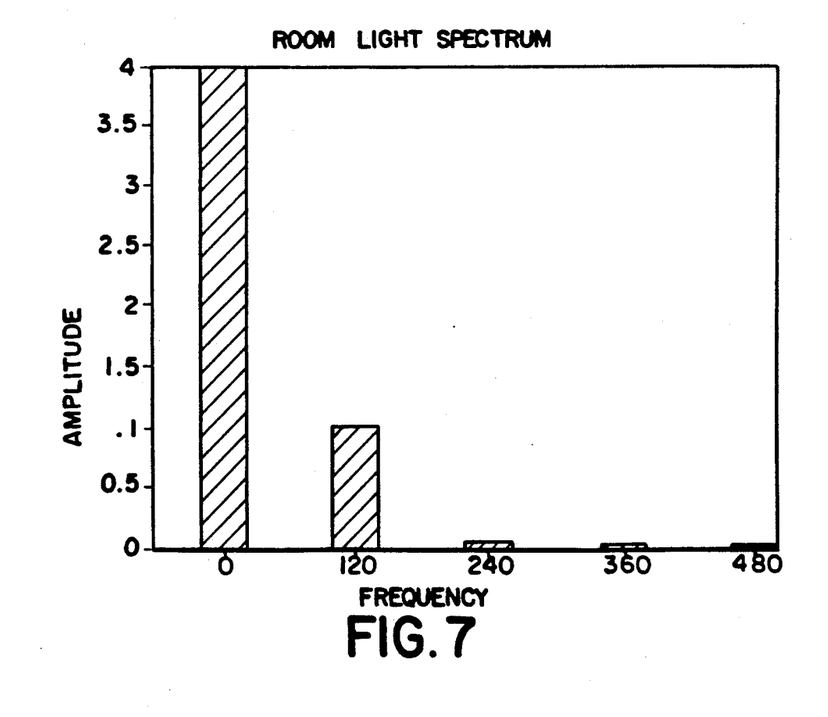

Using the 60 cycle per second frequency found in the power lines of the United States, one could choose a carrier frequency of less than 60 cycles per second, one in-between the harmonics of this frequency: 120, 240, 480, and 960 cycles per second (cps), or one greater than an arbitrary cutoff point of power line harmonic interference. FIG. 7 depicts a hypothetical ambient light spectrum with frequencies of 120, 240, 360 and 480 cps. As is clear from that figure, a carrier frequency above the fourth harmonic would ideally avoid most ambient light harmonic interference.

This principle is equally applicable to power line frequencies outside the United states, such as 50 to 55 cycles per second found in Europe. Several examples of selected frequency ranges are herein provided to serve as a reference:

EXAMPLE 1

Possible ranges for carrier frequencies for a power line frequency of 60 cycles per second:
1. Less than 54 cycles per second.
2. Between 66 and 108 cycles per second.
3. Between 132 and 216 cycles/second.
4. Between 264 and 432 cycles/second.
5. Above 1056 cycles/second.

EXAMPLE 2

Possible ranges for carrier frequencies for a power line frequency of 50 cycles per second:
1. Less than 45 cycles/second.
2. Between 55 and 90 cycles/second.
3. Between 110 and 180 cycles/second.
4. Between 220 and 360 cycles/second.
5. Above 880 cycles per second.

EXAMPLE 3

Possible ranges for carrier frequencies for a power line frequency of 55 cycles per second:
1. Less than 49.5 cycles/second.
2. Between 60.5 and 121 cycles/second.
3. Between 121 and 198 cycles/second.
4. Between 242 and 396 cycles/second.
5. Above 968 cycles/second.

The output of timing circuit 106 is applied to operational amplifier 118, which receives at its other (negative) input a reference voltage from across resistances 120 and 122. The output voltage $V_1$ of operational amplifier 118 is applied across resistor 134 in the form of a square wave at a fixed carrier frequency with the maximum voltage equal to the voltage across resistor 120 and a minimum voltage equal to 0 volts. The driver of the invention further includes an offset control device such as the circuitry behind resistor 130 of FIG. 5 and further described as follows. The output from the digital to analog converter 116 is either +10 volts or 0 volts and is used to determine clock states $\Phi_1$, $\Phi_2$ selected at step 30 of FIG. 2. In a preferred embodiment, a Computer Continuum LAB 40 with a LAB 40-2 12-bit analog to digital module may be used for this purpose. Bit 0 of the 8-bit data output is connected to the operational amplifier 124 for comparison with a reference voltage from across resistances 126 and 128. The output of operational amplifier 124 is then applied across resistor 130 to a summation operational amplifier configuration 144 having a feedback path across resistor 142. Amplifier 144 also receives the voltage $V_1$ after voltage division across resistances 132, 134 and 136 and combines the carrier frequency voltage across resistor 132 with the offset voltage across resistor 130 generated by the digital to analog converter 116 to generate an output voltage $V_2$ at 146 which is a square wave with a frequency $F_c$. Since at clock state the maximum voltage equals 10 volts and the minimum voltage equals 0 volts, while at clock state $\Phi_2$ the maximum voltage equals 0 and the minimum voltage equals $-10$ volts, a buffer operation is also utilized at amplifier 148.

The output of amplifier 148 is applied across resistor 150 to the light-emitting diode current driver section where power transistors 152 and 158 are used to drive the LEDs 160 and 162. In a preferred embodiment, transistor 152 is a TIP 31 and transistor 158 is a TIP 32 transistor. Load resistors 154 and 156 are also used to determine the current and brightness of light-emitting diodes 160 and 162.

Generally, physiology requires that the red light-emitting diode be about twice as bright as the infrared light-emitting diode. Thus, resistor 154 is chosen to deliver about 100 mA to the red light-emitting diode while resistor 156 is chosen to deliver about 50 mA to the infrared light-emitting diode. Attenuating the red light-emitting diode to about 50% yields both intensities near each other at the detector, although this is for convenience and is not a requirement. The two light emitting diodes 160 and 162 are connected in opposite directions as shown so that a current in one direction will illuminate one of the light-emitting diodes and a current in the opposite direction will illuminate the other, thereby producing a pulsing effect. Since the opposed relationship is not a requirement, this device could also employ separate wirings for each LED.

Another embodiment of this light-emitting driver circuit of FIG. 5 may also encompass a calibration device shown by the digital to analog converter 138 and resistor 140 in FIG. 5. A o small sine signal at 1 Hz or other suitable waveform, such as one emulating an arterial pulse applied through D/A converter 138 would produce a signal which would be interpreted at the detector as a pulse. Resistor 140 could be any value to keep the scale appropriate. Such am embodiment also preferably utilizes a voltage across resistor 128 of +12 volts. In addition, potentiometer 112 is preferably adjusted so that the fixed carrier frequency may be kept equal to 47 kHz. Preferably, the operational amplifiers 118, 124, 144 and 148 in this configuration are BiFets, TL074, while the light-emitting diodes 160 and 162 used in this embodiment are those from a Nellcor D-25 Oxisensor.

Sample values of an embodiment of the driver circuit of FIG. 5 include: capacitor 104=88 µf, capacitor 108=0.1 µf and capacitor 11=0.01 µf; resistors 120, 122, 126, 134 and 136=10 KΩ, resistors 132, 142=100 KΩ, resistor 150=100 Ω, resistor 114=135 Ω, resistor 128=4.8 KΩ, resistor 130=220 Kµ, resistor 140 can be preselected, resistor 154=100 Ω and resistor 156=200 Ω.

As noted above with respect to FIG. 3, a linear photodetector 70 is used for detecting the transmitted light from the body tissue of a patient. A linear photodetector is used so that the output of the photodetector is directly proportional to the input as represented by the light emission intensities. For this embodiment, the photodetector used may be Nellcor D-25 Oxisensor, for example. A detailed embodiment of the detector circuitry of FIG. 3 including the photodetector 70 will now be described with respect to FIG. 6.

Figure 6:
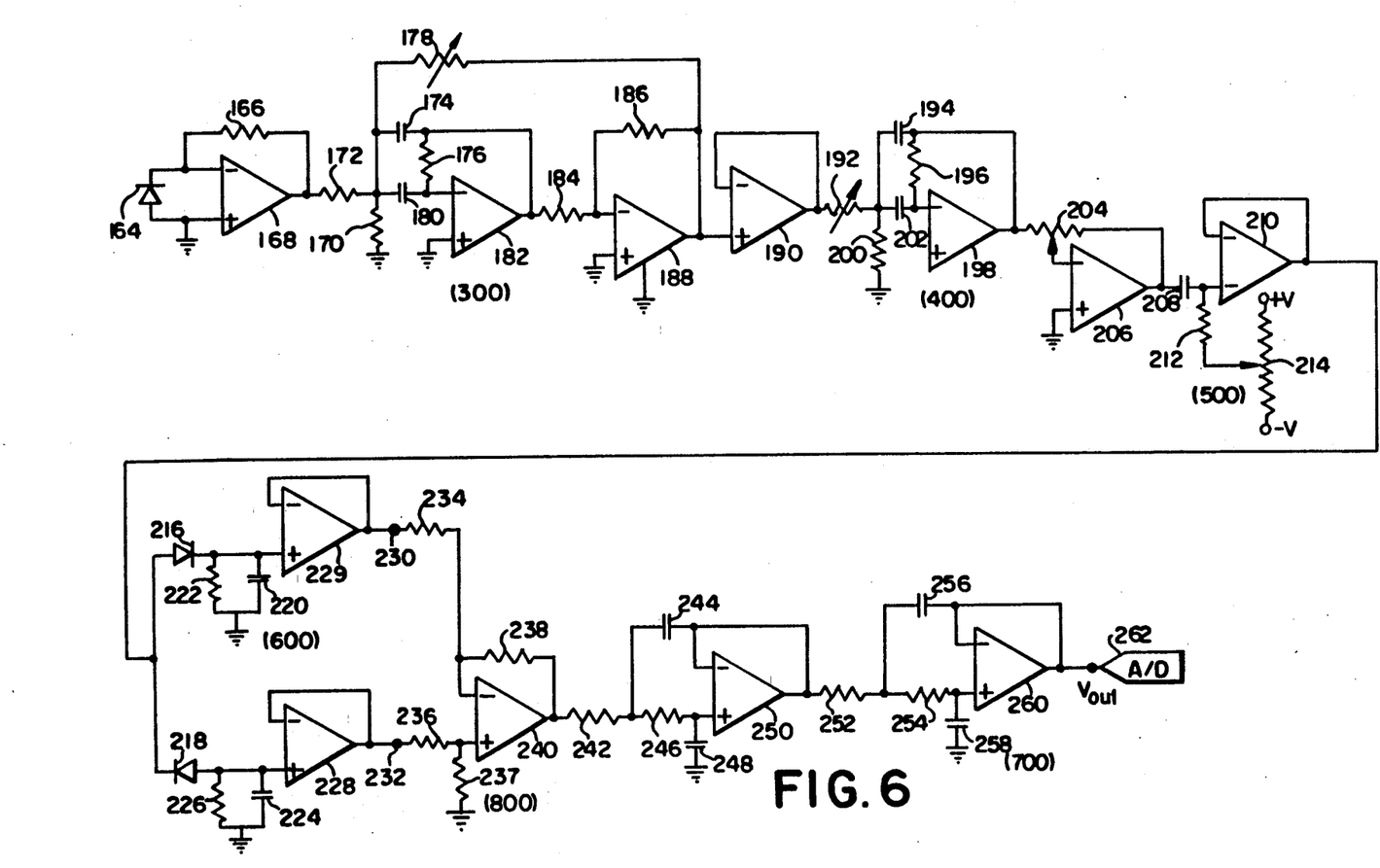
FIG. 6 is a schematic diagram of an embodiment of the receiver circuitry in accordance with a preferred embodiment.

As shown in FIG. 6, photodetector 70 preferably includes a diode 164, resistor 166 and operational amplifier 168. The output of this detector is then applied to a band pass filter circuit, 300 and 400, which is designed to have a center frequency at the carrier frequency $F_c$. As shown, two band pass filters 300 and 400 comprised of elements 170-202 are used, whereby the first band pass filter preferably has a gain equal to 10 and a Q equal to 50 and the second band pass filter 400 preferably has a gain equal to 4, but variable, and a Q equal to 10. In other words, the Q of the filter 300 must be adequate to allow passage of the carrier frequency $F_c$ while rejecting other frequencies in accordance with the AM demodulating technique of the invention for detecting a pulse modulated by the flow of blood. This plurality of band pass filter states enables the device of the invention to filter out noise frequencies while at the same time accepting only the frequency associated with the admitted light intensities of either the red or infrared light. This frequency filtering state acts much like a tuner on a radio in that the band pass filters are matched or tuned to the carrier frequency. Such use of narrow bandwidth devices represents a significant improvement over the wide band AC amplifiers of the prior art for the reasons given in the background portion of the specification.

In addition, by using a narrow band width amplifier as opposed to a wide band amplifier, BOVIE interference, which is created by electronic surgical instruments and can sufficiently cause interference in a range less than 1 kHz but typically affects the frequency range of 0.5 to 5 mHz and can be found even in direct current, can be minimized. Wide band amplifiers pick up the BOVIE signal more readily, thereby creating more error in the clinical environment. Thus, a narrow band amplifier like the one used herein has a much greater chance at eliminating BOVIE interference and can produce a better signal to noise ratio.

As shown in FIG. 6, a variable gain direct current inverting amplifier represented by resistor 204 and operational amplifier 206 follows the band pass filter 400 to allow the user to adjust the overall system gain as appropriate to yield an output voltage which is approximately 8 volts for the larger voltage channel. A calibration adjustment circuit 500 is coupled to operational amplifier 206 across capaciter 208. Calibration adjustment circuit 500 includes an operational amplifier 210, resistor 212 and potentiometer 214 for making the necessary adjustments. If calibrated sufficiently, capacitors 220 and 224 can be removed by adjusting the voltages across potentiometer 214 until the output of operational amplifier 210 is stabilized.

A full Wave rectifier and envelope detector 600 follows calibration circuit 500. Time constants on the envelope detectors located within the full wave rectifier 600 should be less than 1 msec. or less than 10% of "T". This would allow a complete settling time of about 4 msec. or 40% of "T". This allows approximately 60% of "T" for sampling data points. Preferably, the time constant is less than 0.25 in sec. or less than 2.5% of "T". This would allow a complete settling time of 1 msec. or 90% of "T". By way of example, a full wave rectifier 600 may comprise operational amplifiers 228 and 229, diodes 216 and 218, resistors 222 and 226=270 KΩ, and capacitors 220 and 224=3000 pF, which together yield a 1 msec. time constant. Additional settling time requirements may be imposed by the low pass filter section 700 to be described below.

The time constants for the envelope detectors are inversely proportional to the amount of ripple from the carrier frequency such that the smaller the time constant, the larger the ripple detected. Although the ripple can be averaged out later, it will affect accuracy of the instrument to some extent. The ripple (r) is calculated as a function of the driving frequency, the resistance in the envelope detector and the capacitance in the envelope detector as noted by R. E. Smith in *Circuits, Devices, and Systems*, Wiley, New York, Second Edition, 1967, p. 429. The band pass filter circuit, full wave rectifier, and envelope detectors in combination operate on the driver frequency to recover the waves representing detected light intensity values which were previously modulated with the driving frequency. The recovered waves are then amplified by differential amplifier 800, which consists of resistors 234, 236, 237, 238, and operational amplifier 240. Preferably, the differential amplifier 800 has matched components with tolerances of 1%.

The output of differential amplifier 800 is applied across resistor 242 to low pass filter 700. Low pass filter 700 includes two identical low pass filters in series. The low pass filter should have a cutoff frequency low enough to reject ripple from the rectifier by at least −100 dB, yet not so low that the higher harmonics of the pulse waveform are rejected. The other requirement is that the rise time or setting time be fast enough, in the same order as the rectifier circuit 600, so that adequate time is available at the end of each clock state for sampling data points. The minimum settling time filters used in this preferred embodiment are BESSEL filters with damping factors, equal to 0.8659, for example. A two-pole BESSEL filter is preferred with a cutoff frequency of 250 Hz with 98% settling by 1 ms.

The output voltage from the second low pass filter represented by resistor 252, resistor 254, capacitor 256, capacitor 258 and operational amplifier 260 (which is identical to the first low pass filter represented by capacitor 244, resistor 246, capacitor 248 and operational amplifier 250) is connected directly to the analog to digital converter 262. For this embodiment, a COMPUTER CONTINUUM LAB 40 with a LAB 40-2 12-bit analog to digital module may be used for such an A/D converter.

Sample values of an embodiment of the receiver circuit of FIG. 6 include: Resistors: $166=470$ K$\Omega$; $170=15$ K$\Omega$ $172=100$ K$\Omega$; $178=33$ K$\Omega$(variable for gain); $184=100$ K$\Omega$; $186=68$ K$\Omega$; $192=$variable; $196=680$ K$\Omega$; $200=1.5$ K$\Omega$; $204=200$ K$\Omega$; $222=270$ K$\Omega$; $226=270$ K$\Omega$; $234=10.1$ K$\Omega$; $236=10.1$ K$\Omega$; $237=5$ K$\Omega$; $238=5$ K$\Omega$; $242=1$ M$\Omega$; $246=1$ M$\Omega$; $252=1$ M$\Omega$; and $254=1$ M$\Omega$. Capacitors: $174=100$ pf; $180=100$ pf; $194=100$ pf; $202=100$ pf; $208=100$ pf; $220=3,000$ pf; $24=57$ pf; $248=433$ pf; $256=577$ pf; and $258=433$ pf.

The operating principles for calculating the saturation in accordance with the present invention will now be described.

Hemoglobin is actually a concentration of oxyhemoglobin and a concentration of deoxyhemoglobin. Because there are two species present, two different and unique wavelengths of lights must be used to generate two simultaneous equations. A minimum of one wavelength is required for the measurement of each separate blood constituent component. These simultaneous equations model the extinction of light as a function of absorbence and scattering. Since scattering is a function of wavelength, measuring hemoglobin concentration an saturation by including scattering terms decreases the amount of errors which have caused previous oximeters, which relied on absorbence factors, to be inaccurate in certain clinical environments. Such an effect is described by Joseph M. Schmitt in a thesis entitled "Optical Measurement of Blood Oxygen by Implantable Telemetry", 31, 41 (February, 1986), from Standard Electronics Laboratories, where Schmitt describes the effects of scattering coefficients in the implantable telemetry art. Since Schmitt's teachings are relevant to the discussion of calculating oxygen saturation of hemoglobin, that thesis is hereby incorporated by reference as if fully set forth herein.

The detected output data from the receiver circuitry of FIG. 6 is used to calculate a pulse rate and saturation values. The calculation is summarized with respect to FIG. 2 but will now be described in more detail. The calculations will be described with respect to the following variables:

$\Phi_1$, $\Phi_2$: clock states or periods of excitation of the light-emitting diodes;

M: the number of analog to digital conversions or sample data points during a $\Phi$ state lasting for a time T;

T: the duration of a clock state, $\Phi$;

$V_{ir}$: the light intensity reading from the infrared light-emitting diode as measured by the photodetector;

$V_r$: the light intensity reading from the red light-emitting diode as measured by the photodetector;

S[d]: the light intensity measured at diastole, which is the virtual incident intensity for pulse oximetry;

S[s]: the light intensity measured at systole;

S: the fractional oxygen saturation of hemoglobin.

As noted by Schmitt, the general function for the total observed light at an observation point is given by the following equation:

$$S(p) = \Psi_0 \Sigma_{sf} \exp(-\Sigma_t z) R(r) \tag{1.}$$

where:

S(p) = source function or amount of detected light, which is proportional to the fractional oxygen saturation (S) of hemoglobin;

$\Psi_0$ = incident light flux;

$\Sigma_{sf}$ is equal to the modified scattering coefficient of whole blood which equals $\eta \sigma_s (1-H)(1-\mu)$, where $\sigma_s$ is the scattering cross-section, H is the hematocrit fraction of whole blood and $\mu$ is an asymmetry parameter;

$\Sigma_t$ is equal to the sum of modified scattering and absorption coefficients of whole blood and equals $\eta[\sigma_{ao}S + \sigma_{ar}(1-S)] + \Sigma_{st}$;

z = the incremental change in distance due to a pulsatile flow; and

R(r) = function describing radial distribution of light beam intensity which is assumed to be equal to 1 for this discussion.

The more useful saturation determination is arterial hemoglobin saturation. Because at systole there is a rapid inflow of arterial blood, measuring the change in light extinction from late diastole to early systole will facilitate this measurement. These types of oximeters are designated pulse oximeters. For pulse oximetry, S[p] assumes values between S[d], the intensity at late diastole, and S[s], the intensity at early systole. S[s] is the transmitted intensity for pulse oximetry, while S[d] is the virtual incident intensity for pulse oximetry. The optical path, or incremental change because of pulsation or the inflow of arterial blood, also changes its geometry yielding a value of z' at diastole and z" at systole. Thus, two equations can be written for diastole and systole:

$$S(d) = \Psi_0 \Sigma_{sf} \exp(-\Sigma_t z') \tag{2.}$$

$$S(s) = \Psi_0 \Sigma_{sf} \exp(-\Sigma_t z'') \tag{3.}$$

The difference in extinction between diastole and systole is due primarily to the inflow of arterial blood and can be written as:

$$S(d) - S(s) = \Psi_0 \Sigma_{sf} [\exp(-\Sigma_t z') - \exp(-\Sigma_t z'')]. \tag{4.}$$

However, $z''$ equals $z'+z$ where z is the incremental change due to pulsatile flow. Thus, the equation can be rewritten as:

$$S(d)-S(s)=\Psi_0\Sigma_{st}[exp(-\Sigma_t z')-exp(-\Sigma_t z')exp(-\Sigma_t z)], \quad (5.)$$

which equals:

$$S(d)-S(s)=\Psi_0\Sigma_{st}exp(\Sigma_t z')[1-exp(-\Sigma_t z)]. \quad (6.)$$

For any in vivo transducer application, the terms $\Psi_0$, $\Sigma_{st}$, and $exp[-\Sigma_t z']$ will be a constant for a particular clinical situation which we will designate as K for now, where K equals the product of the source function, the incident light flux and $exp(-\Sigma_t Z)$. Then the equation becomes:

$$S(d)-S(s)=K[1-exp([\Sigma_t z])]. \quad (7.)$$

Now it becomes necessary to develop the terms of $\Sigma_t$:

$$S(d)-S(s)/K=[1-exp(-(\sigma_{ao}S+\sigma_{ar}(1-S)+\Sigma_{st}/\eta)\eta z)] \quad (8.)$$

$$[1-(S(d)-S(s)/K]=exp(-(\sigma_{ao}S+\sigma_{ar}(1-S)+\Sigma_{st}/\eta)\eta z) \quad (9.)$$

where:

$\sigma_{ao}$ is equal to the absorption cross section of an isolated red cell containing completely oxygenated hemoglobin;

$\sigma_{ar}$ is equal to the absorption cross section of an isolated red cell containing completely deoxygenated hemoglobin; and $\eta$ is equal to a fraction of red cells per unit volume of whole blood.

In the above equation, only two variables, S and z, are present, for the other terms are constants, some being wavelength dependent. The next step is to take logarithms:

$$ln[1-(S(d)-S(s))/K]=-(\sigma_{ao}S+\sigma_{ar}(1-S)+\Sigma_{st}/\eta)\eta z \quad (10)$$

$$-ln[1-(S(d)-S(s))/K]=(\sigma_{ao}S+\sigma_{ar}(1-S)+\Sigma_{st}/\eta)\eta z \quad (11)$$

$$-ln[1-(S(d)-S(s))/K]/\eta z=(\sigma_{ao}S+\sigma_{ar}(1-S)+\Sigma_{st}/\eta) \quad (12)$$

$$(\sigma_{ar}-\sigma_{ao})S-ln[1-(S(d)-S(s))/K]/\eta z=\Sigma_{st}/\eta+\sigma_{ar} \quad (13)$$

Because there are two variables, two equations or wavelengths are needed:

$$\text{wavelength 1 } (i): \quad -ln[1-(S_i(d)-S_i(s))/K_i]/\eta z + (\sigma_{ari}-\sigma_{aoi})S = \Sigma_{sti}/\eta + \sigma_{ari} \quad (14)$$

$$\text{wavelength 2 } (ii): \quad -ln[1-(S_{ii}(d)-S_{ii}(s))/K_{ii}]/\eta z + (\sigma_{arii}-\sigma_{aoii})S = \Sigma_{stii}/\eta + \sigma_{arii} \quad (15)$$

These are two simultaneous equations in variables S and $1/z$ which are solved by taking the four measurements: $S_i[d]$, $S_i[s]$, $S_{ii}[d]$, $S_{ii}[s]$. The hemoglobin concentration is then used to calculate $\eta$ for correcting the concentration formulae for the number of red blood cells per unit volume of whole blood. Since these equations utilize $\eta$ to calculate the oxygen content, a more accurate means is provided to measure blood constituents of anemic patients.

The following table is used which displays the other constants needed for two hypothetical wavelengths, 910 nm and 660 nm:

|  | 910 nm | 660 nm |
| --- | --- | --- |
| $\sigma_{ao}$ | .1340 | .0357 |
| $\sigma_{ar}$ | .0802 | .3547 |
| $\sigma_s$ | 36.34 | 60.65 |
| $\sigma_{st}$ | .276 | .309 |
| $\mu$ | .9924 | .9949 |

The variable K includes gain factors, but in particular Contains the overall gain factor which will be different for each wavelength channel and will require determination depending upon the hardware configuration. Also, a unit conversion factor must be included since the variables in K contain physiology and measurement parameters, such as S(d). Thus, S(d) and S(s), in whatever units they happen to be, must be converted to physiology terms, i.e., the units in the log expression must cancel. Note further $K_i$ and $K_{ii}$ are neither equal nor do they render $S_i(d)$ and $S_{ii}(d)$ to be equal or $S_i(s)$ and $S_{ii}(s)$ to be equal.

These equations can be solved by methods of linear algebra to determine S. Using techniques of matrix manipulation, a determination is made and then S is calculated by known techniques.

The above process and calculations may, of course, be implemented in a microprocessor. Such a microprocessor will preferably embody a computer program implementing the steps described herein based upon the output signals received from the analog to digital converter 262. The oxygen saturation [S] in the blood can thus be calculated according to equations (14) and (15). The operation of solving the selected equations amounts to multiplying, dividing, adding and subtracting the received variable and the stored constants. A program used in a preferred embodiment of the invention is written in BETTER BASIC [Summit Software Technology, Inc., 1984] and is set forth below. The software has interfacing points with the analog hardware at digital to analog converters 24, 26 and 28 of FIG. 2. The program alternates between the two clock states for setting the output latch digital to analog converter to 10 volts or ground, waiting to the end of the state and sampling only one data point [M=1].

Using an IBM-XT, the program in this preferred embodiment produces a clock state duration, T, of 12 ms. A buffer 44 of a thousand data points are preferably taken for the red and the infrared channels. The buffer 44 is recorded onto a disc for examination by the higher level of software calculations.

The processing next encompasses calculating the saturation value S using the equations (14) and (15) as previously discussed. An average saturation may be calculated as appropriate at this point in the processing.

As is apparent from the above, the driving signal used to vary the amplitude of an LED output within each clock state is not a clocking signal in the traditional sense, i.e., it does not function to alternatively activate two or more LEDs. In the present device a second signal produced by the clocking means is superimposed as the driving signal for performing this function. Increases in the frequencies of prior art clocking signals would not accomplish the results disclosed herein because such increases would require the use of extremely wide band amplifiers in the receiver, and thus, would not improve, and may decrease, the signal to noise ratio of the device.

From the foregoing it can be realized that this invention provides an improved device and method for blood constituent measurement. The advantages over the prior art are: improved duty cycle, more accurate modeling by using scattering in addition to absorbance parameters, and higher accuracy in the clinical environment by accounting for red blood cell count and by filtering out of ambient light, BOVIE interference, and system noise. Although apparatus have been illustrated, this was for the purpose of describing, but not limiting, the invention. Various modifications, which will become apparent to one skilled in the art, are possible within the scope of this invention. For example, the techniques of the invention may be used to measure concentrations or saturations of other blood constituents such as pulse rate and need not be limited to oxygen saturation.

What is claimed is:

1. A device for non-invasive measurement of arterial blood constitutes for use in an environment generally illuminated by artificial light, comprising:
   driver means for generating a driving signal at a driving signal frequency not substantially present in said artificial light;
   light source means responsive to said driving signal for transmitting light, having respective predetermined wavelengths, at said driving signal frequency through a body tissue of a patient so as to detect said arterial blood constituents;
   selecting means for selectively activating said light source means for predetermined time periods at each of said respective predetermined wavelengths, said predetermined time periods being defined by at least two successive cycles of said driving signal;
   means for applying said driving signal to said light source means during said predetermined time periods so as to cause said light source means to transmit light having said respective predetermined wavelengths at said driving signal frequency through said body tissue of said patient for said at least two successive cycles of said driving signal;
   detecting means for detecting at least said light transmitted through said body tissue of said patient at said driving signal frequency during said predetermined time periods and outputting a detection signal;
   demodulating means tuned to a narrow band receiving frequency range including said driving signal frequency for demodulating said detection signal from said driving signal so as to get a demodulated output representing the concentration of said blood constituents detected by light at said respective predetermined wavelengths, said narrow band receiving frequency range excluding frequencies substantially present in said artificial light; and
   processing means for producing an output proportional to the concentration of said arterial blood constituents from said demodulated output.

2. A device as in claim 1, wherein said processing means further includes means for producing an output proportional to the concentration of saturated hemoglobin oxygen from said demodulated output.

3. A device as in claim 1, wherein said driving signal frequency is modulated by a patient's pulse and said demodulating means further includes means for demodulating said patient's pulse from said driving signal.

4. A device as in claim 1, wherein said light source means comprises first and second light emitting diodes.

5. A device as in claim 4, wherein said driver means generates a square wave which is applied to said first and second light emitting diodes as said driving signal and said selecting means biases said square wave to cause said first light emitting diode to be activated when said square wave is at a first biased level and said second light emitting diode to be activated when said square wave is at a second biased level.

6. A device as in claim 5, wherein said first light emitting diode emits red light and said second light emitting diode emits infrared light.

7. A device as in claim 6, wherein said first and second light emitting diodes are connected to said driver means in relatively reversed polarities such that said driver means applies said driving signal to only one of said light emitting diodes at any given instant in time.

8. A device as in claim 7, wherein said driver means comprises intensity adjustment means for driving one of said light emitting diodes to produce a higher light intensity than the other of said light emitting diodes.

9. A device as in claim 8, wherein said intensity adjustment means drives said first light emitting diode at an intensity of about 1.5 to 2.5 times the intensity of said second light emitting diode.

10. A device as in claim 1, wherein said detecting means comprises a photodetector placed in proximity with said body tissue of said patient so as to detect said light transmitted through said body tissue of said patient, said photodetector producing an output proportional to the intensity of light incident thereon as said detection signal.

11. A device as in claim 1, wherein said demodulating means includes a bandpass filter having a center frequency approximately equal to the frequency of said driving signal.

12. A device as in claim 11, wherein said demodulating means further comprises at an output of said bandpass filter a full wave rectifier and an envelope detector for separating detected signals at said detection frequency from detected signals at the frequency of said driving signal.

13. A device as in claim 12, wherein said demodulating means further comprises at an output of said envelope detector a low pass filter for eliminating ripple from detected signals at said detection frequency.

14. A device as in claim 13, wherein said demodulating means further comprises means for adjusting the gain of said demodulated output.

15. A device as in claim 1, wherein said driving signal is a uniform square wave at 47 kHz.

16. A device as in claim 1, wherein said frequency of said driving signal is greater than the frequency of the fourth harmonic of the frequency of greatest amplitude in said artificial light.

17. A device as in claim 1, wherein said frequency of said driving signal exceeds 1 kHz.

18. A device as in claim 17, wherein said frequency of said driving signal exceeds 5 kHz.

19. A device as in claim 18, wherein said frequency of said driving signal exceeds 10 kHz.

20. A device as in claim 19, wherein said frequency of said driving signal exceeds 40 kHz.

21. A device as in claim 1, wherein said frequency of said driving signal is in-between harmonics of said artificial light.

22. A device as in claim 1, wherein said processing means comprises means for correcting its output in accordance with the fraction of red blood cells per unit volume of whole blood of said patient.

23. A device as in claim 22, wherein said processing means comprises means for waiting for transients to settle before sampling said demodulated output.

24. A device as in claim 23, wherein said processing means comprises means for averaging samples of said demodulated output.

25. A device as in claim 1, wherein said driving signal is a non-periodic repetitive waveform.

26. A device as in claim 1, wherein said driving signal is a sum of at least two sine waves of different frequencies.

27. A method of non-invasive measurement of arterial blood constituents for use in an environment generally illuminated by artificial light, comprising the steps of:
generating a driving signal at a driving signal frequency not substantially present in said artificial light;
selectively activating a light source for predetermined time periods defined by at least two successive cycles of said driving signal;
applying said driving signal to said light source during said predetermined time periods so as to cause said light source to transmit light having respective predetermined wavelengths through a body tissue of a patient at said driving signal frequency for said at least two successive cycles of said driving signal so as to detect said arterial blood constituents;
detecting said light transmitted through said body tissue of said patient at said driving signal frequency during said predetermined time periods and outputting a detection signal;
demodulating in a narrow band receiving frequency range including said driving signal frequency said detection signal from said driving signal so as to get a demodulated output representing the concentration of said blood constituents detected by light at said respective predetermined wavelengths, said narrow band receiving frequency range excluding frequencies substantially present in said artificial light; and
determining an output proportional to the concentration of said arterial blood constituents from said demodulated output.

28. A method as in claim 27, comprising the further step of determining an output proportional to the concentration of saturated hemoglobin oxygen from said demodulated output.

29. A method as in claim 27, wherein said driving signal frequency is modulated by a patient's pulse and said demodulating step further includes the step of demodulating said patient's pulse from said driving signal.

30. A method as in claim 27, comprising the further step of adjusting the intensity of said light source so that light detected in said detecting step is in range of a detector.

31. A method as in claim 27, comprising the further step of bandpass filtering said detection signal in a narrow frequency band about the frequency of said driving signal.

32. A method as in claim 27, wherein said light source comprises first and second light emitting diodes and said driving signal generated in said generating step is a square wave.

33. A method as in claim 32, wherein said selectively activating step includes the step of biasing said square wave to cause said first light emitting diode to be activated when said square wave is at a first biased level and said second light emitting diode to be activated when said square wave is at a second biased level.

34. A method as in claim 33, wherein said demodulating step includes the step of separating detected light at the frequency of said first light emitting diode from detected light at the frequency of said second light emitting diode.

35. A method as in claim 34, wherein said determining step includes the step of determining the concentration of said arterial blood constituents from the demodulated output at the frequencies of said first and second light emitting diodes.

36. A method as in claim 35, comprising the further step correcting the determined concentration of said arterial blood constituents in accordance with the fraction of red blood cells per unit volume of whole blood of said patient.

37. A device for non-invasive measurement of arterial blood constituents for use in an environment generally illuminated by artificial light, comprising:
driver means for generating a driving signal at a driving signal frequency not substantially present in said artificial light;
light source means responsive to said driving signal for transmitting light, having first and second predetermined wavelengths, at said driving signal frequency through a body tissue of a patient so as to detect said arterial blood constituents;
means for establishing first and second time periods during which said light at said first and second predetermined wavelengths are to be respectively transmitted, said first and second time periods each comprising at least two successive cycles of said driving signal;
means for applying said driving signal to said light source means for causing said light source means to transmit light at said first detection frequency through said body tissue of said patient during said first time period for at least two successive cycles of said driving signal and at aid second detection frequency through said body tissue of said patient during said second time period for at least two successive cycles of said driving signal;
detecting means for detecting at least said light transmitted through said body tissue of said patient at said driving signal frequency during said first and second time periods and outputting a detection signal;
demodulating means tuned to a narrow band receiving frequency range including said driving signal frequency for demodulating said detection signal from said driving signal so as to get a demodulated output substantially independent of the level of said artificial light and representing the concentration of said blood constituents detected by light at said first and second predetermined wavelengths, said narrow band receiving frequency range excluding frequencies substantially present in said artificial light; and processing means for producing an output proportional to the concentration of said arterial blood constituents from said demodulated output.

38. A device as in claim 37, wherein said processing means comprises means for producing at least an output which is proportional to an oxygen content of the patient's blood.

39. A device as in claim 37, wherein the driving signal frequency is greater than the frequency of a fourth harmonic of a supply frequency to the artificial light.

40. A device as in claim 37, wherein the driving signal frequency comprises a frequency in which is located in-between a pair of adjacent harmonics of a supply frequency to the artificial light.

41. A device as in claim 37, wherein the driver means is matched to the detecting means with respect to the driving signal frequency for allowing passage of the driving signal frequency and rejecting other frequencies.

42. A device as in claim 41, wherein the detecting means comprises a filter for allowing passage of the driving signal frequency and for rejecting other frequencies.

43. A device as in claim 37, wherein the processing means comprises means for generating a correction signal which is proportional to the fraction of red blood cells per unit volume of whole blood and for correcting for an altered extinction of light due to scattering which is proportional to a reduced blood cell count.

* * * * *

UNITED STATES PATENT AND TRADEMARK OFFICE
CERTIFICATE OF CORRECTION

PATENT NO. : 5,193,543
DATED : MARCH 16, 1993
INVENTOR(S) : MARK YELDERMAN

It is certified that error appears in the above-indentified patent and that said Letters Patent is hereby corrected as shown below:

Column 2, line 61, "Which" should be "which".

Column 8, line 37, after "0 volts." start a new paragraph with "The".

Column 9, line 22, after "A" delete "o".

Column 9, line 38, "capacitor 11" should be "capacitor 110".

Column 9, line 41, "4.8" should be "48".

Column 11, line 32, "KΩ172" should be "KΩ; 172".

Column 11, end of line 52, "an" should be "and".

Column 18, line 49, "aid" should be "said".

UNITED STATES PATENT AND TRADEMARK OFFICE
CERTIFICATE OF CORRECTION

PATENT NO. : 5,193,543
DATED : March 16, 1993
INVENTOR(S) : Mark Yelderman

It is certified that error appears in the above-indentified patent and that said Letters Patent is hereby corrected as shown below:

Column 19, line 14, delete "in".

Signed and Sealed this

Twenty-second Day of March, 1994

Attest:

BRUCE LEHMAN

Attesting Officer  Commissioner of Patents and Trademarks